United States Patent [19]

Schmidt-Dunker

[11] 4,134,969
[45] Jan. 16, 1979

[54] METHOD OF TREATMENT OF CALCIUM DISORDERS USING AMINOALKANE-DIPHOSPHONIC ACIDS

[75] Inventor: Manfred Schmidt-Dunker, Düsseldorf, Germany

[73] Assignee: Henkel Kommanditgesellschaft auf Aktien (Henkel KGaA), Dusseldorf-Holthausen, Germany

[21] Appl. No.: 672,561

[22] Filed: Mar. 12, 1976

Related U.S. Application Data

[62] Division of Ser. No. 529,039, Dec. 3, 1974, Pat. No. 3,962,432.

[30] Foreign Application Priority Data

Feb. 4, 1974 [DE] Fed. Rep. of Germany ....... 2405245

[51] Int. Cl.$^2$ ................................................ A61K 7/22
[52] U.S. Cl. ........................................ 424/49; 424/48; 424/204
[58] Field of Search .................... 424/204, 49, 57, 48; 260/932

[56] References Cited

U.S. PATENT DOCUMENTS

| 3,442,604 | 5/1969 | Smith et al. ............................ 424/204 |
| 4,054,598 | 10/1977 | Blum et al. ......................... 424/49 X |

OTHER PUBLICATIONS

Krueger et al., Ger. Offen, Chem. Abstracts, vol. 78, 1973, p. 451, parag. 84528z.

*Primary Examiner*—Richard Raymond
*Attorney, Agent, or Firm*—Hammond & Littell

[57] ABSTRACT

A method for the treatment of diseases relating to the abnormal deposition or dissolution of difficultly soluble calcium salts in the body or mouths of warm-blooded animals which consists of administering orally, parenterally or topically to said warm-blooded animals, a safe but effective amount of at least one pharmacologically acceptable aminoalkane diphosphonic acid derivative or a water-soluble salt thereof.

4 Claims, No Drawings

METHOD OF TREATMENT OF CALCIUM DISORDERS USING AMINOALKANE-DIPHOSPHONIC ACIDS

This is a division of Ser. No. 529,039, filed Dec. 3, 1974, now U.S. Pat. No. 3,962,432.

A number of diseases are known in human and veterinary medicine which are associated primarily or partly with the abnormal deposition or dissolution of difficulty soluble calcium salts in the animal body. These diseases can be divided into two categories:

(1) Abnormal depositions of difficulty soluble calcium salts, mostly calcium phosphate which, cause bone malformations, pathological hardening of tissues and secretions in organs;

(2) The abnormal dissolution of hard tissues, which causes losses of hard bone substance which cannot be replaced or which are replaced only by incompletely crystallized tissue. This dissolution is frequently accompanied by pathologically high calcium and phosphate concentrations in the plasma.

In the first category belong diseases like arthritis, neuritis, bursitis, tendonitis and other inflammatory diseases where the deposit of calcium phosphate is enhanced in the respective body parts. Hyperparathyroidism caused by hormonal disorders can, in combination with hypercalcemia, produce a calcium deposit in many organs. Myositis ossificans (fibrodysplasia) leads to progressive ossification of the musculature, and in Bechterew's disease, a typical inflammatory disorder of the bone joint system, progressive calcification leads to an ossification of the entire vertebral system.

Particularly frequent among the diseases of the first category is arteriosclerosis, where calcification of the aorta and of the arteries appears as a rule in the progressive stage. Furthermore, calculi of all kinds belong here, like kidney stones, gall stones, bladder stones and sialolith (tartar). Even though these stones do not consist completely of calcium phosphate, a calcium phosphate deposit can be assumed in most cases as a nucleus.

To the second category of diseases belong hereditary hypophosphatasia as well as osteoporosis, where there is insufficient reformation of bone substance for various reasons (senile, menopausal, caused by treatment with drugs like steroids, or by diseases, like arthritis). Furthermore, this group comprises Paget's disease (*Osteitis deformans*) where the dissolution of normal bone substance is accompanied by reformation of soft, only slightly crystallized tissue, as well as Osteodystrophia fibrosa generalisata, a systemic disease with irregular bone disintegration.

A number of these diseases appear relatively frequently in human, as well as in veterinary medicine. A completely satisfactory therapy for these diseases has not yet been described, though controlled diets, treatment with fluorides, phosphates or condensed phosphates, with sex hormones, and particularly with the hormone calcitonin have been suggested and also used. In the last years the treatment of some of these diseases with phosphonates has been suggested. In addition U.S. Pat. No. 3,584,124 suggests treating some of these diseases with ethane-1,2-dihydroxy-1,2-dicarboxy-1,2-diphosphonic acid and its salts.

It has also been suggested to add chemical substances to oral hygiene products and dentrifices in order to prevent the deposition and cause the dissolution of the difficulty soluble calcium salts known as tartar. Such deposits are frequently removed by mechanical means.

As chemically active agents, compounds like ethylene diamine tetraacetic acid or nitrilo-triacetic acid have been added to toothpaste, mouthwashes or special ointments. While these toothpastes and mouthwashes serve primarily for the prophylactic treatment of tartar formation, special ointments, which are applied to the teeth and remain there for some time, have the function of removing the tartar or at least making it easier to remove. But these products have not been greatly used in practice so far, because they must meet a number of different requirements. First, such cosmetic preparations must be pharmacologically harmless, particularly since they can be accidentally swallowed. The agents should prevent the formation of tartar without destroying the tooth structure. Besides, they must not cause any irritation of the gums or of the mucous membrane of the mouth.

An object of the present invention is the development of therapeutic methods and pharmacological preparations which may be utilized in the treatment of the above conditions.

Another object of the present invention is the development of a method for the treatment of diseases relating to the abnormal deposition or dissolution of difficultly soluble calcium salts in the body or mouths of warm-blooded animals which consists of administering orally, parenterally or topically to said warm-blooded animals, a safe but effective amount of at least one pharmacologically acceptable aminoalkane-diphosphonic acid derivative or a water-soluble salt thereof.

A further object of the present invention is the development of a pharmaceutical composition consisting essentially of a minor amount of at least one pharmacologically acceptable aminoalkane-diphosphonic acid derivative or a water-soluble salt thereof, and a major amount of pharmacologically acceptable excipients.

These and other objects of the present invention will become more apparent as the description thereof proceeds.

The invention concerns pharmaceutical or cosmetic preparations to influence the deposition and dissolution of difficultly soluble calcium salts by using certain aminoalkane diphosphonic acids or their nontoxic pharmacologically acceptable water-soluble salts as an active ingredient, as well as the method of using the acids or their salts to influence this deposition or dissolution of these difficultly soluble calcium salts.

It was found that aminoalkane-diphosphonic acids or their water-soluble salts are suitable for the therapeutic treatment of disorders of calcium or phosphate metabolism and of diseases caused by them. The new pharmaceutical or cosmetic products for influencing the deposition and dissolution of difficultly soluble calcium salts are, therefore, characterized by the fact that they contain as an active ingredient a nontoxic effective amount of an aminoalkanediphosphonic acid of the formula

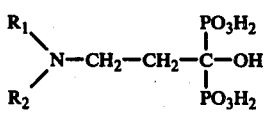

or the nontoxic pharmacologically acceptable water-soluble salts, where $R_1$ and $R_2$ are hydrogen or alkyl having 1 to 3 carbon atoms. Specifically all the compounds indicated in Table I below are suitable, but 3-amino-1-hydroxypropane-1,1-diphosphonic acid is preferred.

More particularly, therefore, the present invention relates to a method for the treatment of diseases relating to the abnormal deposition or dissolution of difficultly soluble calcium salts in the body or mouths of warm-blooded animals which consists of administering orally, parenterally or topically to said warm-blooded animals, a safe but effective amount for said treatment of at least one pharmacologically acceptable aminoalkane-diphosphonic acid derivative selected from the group consisting of (A) at least one aminoalkane-diphosphonic acid of the formula

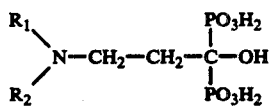

wherein $R_1$ and $R_2$ are each selected from the group consisting of hydrogen and alkyl having 1 to 3 carbon atoms, and (B) a nontoxic pharmacologically acceptable water-soluble salt of (A); as well as a pharmaceutical composition consisting essentially of a minor amount of at least one pharmacologically acceptable aminoalkane diphosphonic acid derivative mentioned above and a major amount of pharmacologically acceptable excipients.

The aminoalkane-diphosphonic acids of the above mentioned type can be obtained by reacting β-alanine or β-alanine alkylated on the nitrogen atom with phosphorus trichloride and phosphorous acid. The reaction can take place in the presence or absence of an organic diluent.

Specific examples of these aminoalkane-diphosphonic acids are
3-amino-1-hydroxypropane-1,1-diphosphonic acid,
3-(dimethylamino)-1-hydroxypropane-1,1-diphosphonic acid,
3-(diethylamino)-1-hydroxypropane-1,1-diphosphonic acid,
3-(dipropylamino)-1-hydroxypropane-1,1-diphosphonic acid,
3-(ethylpropylamino)-1-hydroxypropane-1,1-diphosphonic acid,
3-(methylamino)-1-hydroxypropane-1,1-diphosphonic acid,
3-(ethylamino)-1-hydroxypropane-1,1-diphosphonic acid, and
3-(propylamino)-1-hydroxypropane-1,1-diphosphonic acid.

Table I below sets forth the formulae for the above-mentioned compounds.

TABLE I

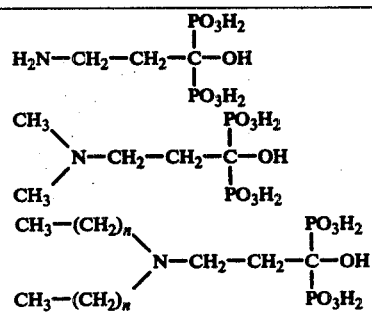

TABLE I-continued wherein n is an integer from 1 to 2

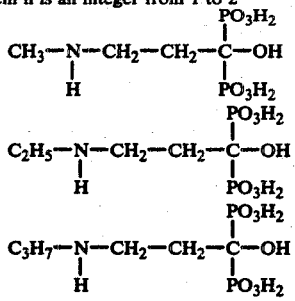

Instead of the free acid, its pharmacologically acceptable, water-soluble salts, for example, the alkali metal salts such as the sodium or potassium salts, the magnesium salts, the ammonium salts and substituted ammonium salts, such as lower alkylammonium and lower alkanolammonium salts, such as mono-, di- or triethanol-ammonium salts can also be used. For pharmaceutical applications, both the partial salts, in which only a part of the acid proton is substituted by other cations and full salts can be used, but partial salts which react substantially neutral in aqueous solution (pH 5 to 9) are preferred. Mixtures of the above salts can also be employed.

The dosage range of the aminoalkane-diphosphonic acid derivatives is variable and depends on the respective conditions, such as the type and severity of the disease, duration of the treatment, and the particular compound being utilized. Individual dosages can be from 0.05 to 500 mg per kg of the warm-blooded animal body weight. The preferred dose is 1 to 50 mg per kg of body weight, and can be administered up to four times daily. The higher doses are necessary for oral application, due to the limited resorption. In longer treatments, after initial higher doses, lower doses are normally required to maintain the desired effect.

Doses under 0.05 mg per kg of body weight have little effect on the pathological calcification or dissolution of hard tissue. Doses above 500 mg/kg of body weight may have toxic side effects in the long run. The aminoalkane-diphosphonic acid derivatives or their salts can be administered orally, and, in hypertonic solution, subcutaneously, intramuscularly and intravenously in the form of tablets, pills, capsules or as injectable solutions. For certain animals these aminoalkane-diphosphonic acid derivatives can also be used as part of the feed or of feed additives.

The preferred dosage for these various methods of administration are, in mg/kg:

| Orally | 1 to 50 |
|---|---|
| Subcutaneously | 1 to 10 |
| Intramuscularly | 0.05 to 10 |
| Intravenously | 0.05 to 2 |

The aminoalkane-diphosphonic acid to be used according to the invention is generally added in the form of its alkali metal salts to the corresponding oral hygiene products and dentrifices, such as toothpastes, mouthwashes, tooth cleaning powders, mouth lozenges, chewing gum, and tooth treatment ointments in amounts of 0.01% to about 5% by weight. Oral hygiene products which are necessarily swallowed, like mouth lozenges and chewing gum, should only contain small amounts of up to about 1% by weight; those that are frequently swallowed by accident should not contain more than about 2.5% by weight. The highest amounts can be incorporated in tooth treatment ointments which are used locally by the dentist for the treatment of acute cases.

The pH value of the oral hygiene products and dentrifices according to the invention can range from 5 to 9. The lower limit should not be set lower for safety reasons, to prevent damage to the tooth enamel in a combination of unfortunate circumstances, despite the great safety in the treatment with aminoalkane-diphosphonic acid. The upper limit results from practical considerations, since it is not possible to product alkaline products which are satisfactory in aroma and taste.

The suitability of the aminoalkane-diphosphonic acid derivatives to be used according to the invention for the therapeutic and prophylactic treatment of tartar results from its capacity of inhibiting even in small amounts crystallization in the precipitation of calcium apatite. Calcium-apatite, which is precipitated in the presence of aminoalkane-diphosphonic acid, is X-ray amorphous, in contrast to crystalline apatite which is usually formed without this addition.

In mouthwashes, a combination with the aqueous-alcoholic solution of various types of essential oils, emulsifiers, wetting agents, antiseptics, astringents and tonicizing drug extracts, caries-preventing additives, and flavor correctives can be readily used. Hydrogen peroxide-containing mouthwashes, which can be used to prevent paradontosis, can also be provided with the additive according to the invention.

The toothpastes are generally pasty preparations of water, thickeners, wetting and foaming agents, moisturizers, abrasives, scouring and cleaning agents, aromas, flavor corrective, antiseptics and other valuable oral-cosmetic substances. The cleaning agents and other additives to be used in the toothpastes according to the invention should, as far as possible, be free of soluble calcium in order not to impair the tartar-preventing action of the aminoalkane-diphosphonic acids.

The cleaning agents are, therefore, primarily secondary calcium phosphate, sodium metaphosphate, precipitated silicas, aluminum silicates, calcium pyrophosphate, and finely dispersed synthetic resins, like melamine-urea-formaldehyde resins or polylower alkylmethacrylates. The content of cleaning agent in the toothpastes is generally between 25 and 60%. The wetting and foaming agents used are primarily soap-free anionic surface-active compounds, like fatty alcohol sulfates, e.g., sodium lauryl sulfate, monoglyceride sulfides, sodium lauryl sulfoacetate, sarcosides, taurides and other anionic surface-active compounds which do not influence the taste in amounts of 0.5% to 5%. For the production of the binder for the toothpastes, all thickeners that are customary for this purpose can be used, like hydroxyethyl cellulose, sodium carboxymethyl cellulose, tragacanth, carragheen, agar, gum arabic, as well as additional finely dispersed silicas. The moisturizers are primarily glycerin and sorbitol in amounts of up to about one-third of the total agent. The desired aroma and flavor can be achieved by the addition of essential oils, like peppermint, clover, wintergreen or sassafras oil, as well as sweetening agents, like saccharin, dulcin, dextrose, levulose, etc. In addition, caries-preventing additives, like fluorides or fluorphosphates can be used. The content of the tartar-preventing aminoalkane-diphosphonic acid to be used in the toothpastes according to the invention is between 0.01 and 5%, particularly 1% and 4%, related to the total mass of the toothpaste.

The activity of the compounds listed in Table I and particularly of 3-amino-1-hydroxypropane-1,1-diphosphonic acid or a nontoxic pharmacologically acceptable water-soluble salt of the above mentioned compounds is probably due to an interaction of the phosphonic acid with the crystal surface of the calcium phosphate.

The effects that can be achieved with the new pharmaceutical preparations can be demonstrated by the tests and applications described in the following examples. These examples are illustrative of the practice of the invention without being limitative thereof in any respect.

EXAMPLE 1

Apatite Crystallization Delay Test in Vitro

The compounds utilized according to the invention are efficient in preventing abnormal calcium depositions. Their efficacy in this respect was demonstrated in vitro by their retarding the crystallization of apatite.

Supersaturated solutions of $Ca^{++}$ and $HPO_4^{--}$ ions are relatively stable, but crystallize after the addition of apatite nuclei according to the reaction $$5\,Ca^{++} + 3\,HPO_4^{--} + H_2O \rightarrow Ca_5(PO_4)_3OH + 4\,H^+$$

with the release of protons. The reaction can, therefore, be readily observed by titration with a base at a constant pH.

400 ml of 0.0008 molar $KH_2PO_4$ solution were mixed with 45 ml of a 0.012 molar $CaCl_2$ solution, and the clear solution was standardized with KOH to a pH of 7.4, after being brought to a temperature of 35° C. After 30 minutes during which time the pH did not change, a suspension of 100 mg of hydroxyl apatite in 50 ml of $H_2O$ was added. The crystallization set in immediately and was followed by "pH-Stat" titration with 0.05 N KOH.

If a small amount of one of the aminoalkane-diphosphonic acids of the invention, and particularly 3-amino-1-hydroxypropane-1,1-diphosphonic acid was added to the solution before the apatite was added, the crystallization was greatly delayed. The inhibition of the crystallization was 75% after 8 hours at a concentration of 4 mg/l, and 90% after 8 hours at a concentration of 20 mg/l. Even after 14 hours the values are still considerably lower than those of the test without the addition of inhibitors.

EXAMPLE 2

Retardation of the Dissolution of Calcium Hydroxyl Apatite

The dissolution of calcium hydroxyl apatite crystals in a solution buffered to pH 7.0 is delayed by small amounts of 3-amino-1-hydroxypropane-1,1-diphosphonic acid. This can be shown by the following test.

50 ml of a 0.1 molar sodium barbital solution (prepared by dissolving 18.42 gm of 5,5-diethyl-barbituric acid with 0.1 mol of NaOH in 1 liter of water) were mixed a weighed amount of 3-amino-1-hydroxypropane-1,1-diphosphonic acid. The solution was diluted to 450 ml and brought to a pH of 7.0 with 0.1 N HCl.

Subsequently, 5.78 gm of KCl were added and the solution is brought to exactly 500 ml.

1 gm of hydroxyl apatite was added to the buffer solution thus prepared, and the suspension was stirred in a closed bottle for 15 hours at 25° C. After filtration through a Millipore filter (pore with 1 to 2 μm), the clear solution was concentrated to 100 ml, and calcium oxalate was precipitated with the addition of 20 ml of a saturated sodium oxalate solution. The precipitate was centrifuged off. The residue was brought into solution with 10 ml of fuming nitric acid and the calcium in the aqueous solution was titrated by complexometry.

The following values were reported below in Table II.

TABLE II

| 3-Amino-hydroxypropane-1,1-diphosphonic acid (mg) | Calcium (mg/l) | % Reduction of the dissolution |
|---|---|---|
| 0 | 16.0 | — |
| 5 | 15.4 | 3.8 |
| 10 | 10.5 | 33.8 |
| 20 | 9.8 | 38.8 |

With a concentration of 40 mg of the 3-amino-1-hydroxypropane-1,1-diphosphonic acid in 1 liter of the apatite suspension, a 40% reduction of the dissolution was obtained.

EXAMPLE 3

Prevention of Hardening of the Aorta in Rats

The effectiveness of the aminoalkane-diphosphonic acids particularly 3-amino-1-hydroxypropane-1,1-diphosphonic acid in preventing abnormal calcium deposits in vivo in rats can be demonstrated as follows.

This test was based on the observation that high doses of Vitamin $D_3$ cause a considerable hardening of the aorta in rats. 30 Female rats weighing 150 to 200 gm each were divided into three groups of 10 animals each. They received during the test period of normal diet and tap water and libitum. One group of 10 animals (control) received no further treatment. Another group of the animals received from 3rd to the 7th day, 75,000 units of vitamin $D_3$ daily through a stomach sound. The third group likewise received from the 3rd to the 7th day, 75,000 units of vitamin $D_3$ daily through a stomach sound and, in addition, likewise orally, 10 mg per kg of 3-amino-1-hydroxypropane-1,1-diphosphonic acid from the 1st to the 10th day. After 10 days the animals were sacrificed and their aortas prepared and dried for 12 hours at 105° C. After determination of the dry weight, the aortas were ashed; the residue was dissolved, and the calcium was determined by flame photometry. The treatment with 3-amino-1-hydroxypropane-1,1-diphosphonic acid reduced the vitamin $D_3$ induced hardening of the aortas of rats considerably.

In Examples 1 to 3, comparable results were obtained when any one of the other 3-amino-1-hydroxypropane-1,1-diphosphonic acids listed in Table I, or a nontoxic pharmacologically acceptable water-soluble salt, either the partial salt or the complete salt, were substituted for the specific compound utilized in these examples. Specific examples of these salts include the sodium salt, potassium salt, magnesium salt, ammonium salt, or the mono-, di- or triethanol ammonium salt.

The following examples 4 and 5 illustrate a few dosage unit compositions comprising a compound used according to the present invention as an active ingredient.

EXAMPLE 4

Capsules

The capsule filler composition was compounded by known methods from the following ingredients:

| | |
|---|---|
| 3-Amino-1-hydroxypropane-1,1-diphosphonic acid | 100 mg |
| Starch | 20 mg |
| Sodium lauryl sulfate | 1 mg |

The capsule contained an effective dosage unit composition for the treatment of diseases relating to the abnormal deposition or dissolution of difficultly soluble calcium salts in a warm-blooded animal.

EXAMPLE 5

Tablets

The tablet composition was compounded by known methods from the following ingredients:

| | |
|---|---|
| Disodium salt of 3-amino-1-hydroxypropane-1,1-diphosphonic acid | 100 mg |
| Lactose | 100 mg |
| Starch | 47 mg |
| Magnesium stearate | 3 mg |

Each tablet contained an effective dosage unit composition for the treatment of diseases relating to the abnormal deposition or dissolution of difficultly soluble calcium salts in a warm-blooded animal.

Analogous results are obtained when any one of the other compounds listed in Table I or a non-toxic pharmacologically acceptable water-soluble, partial or complete, salt thereof is substituted for the particular compound in Examples 4 and 5. Likewise, the amount of active ingredient in these illustrative examples may be varied to achieve the desired dosage unit range and the amounts and nature of the inert pharmaceutical carrier ingredients may be varied to meet particular requirements.

EXAMPLE 6

Oral Preparations

When 3-amino-1-hydroxypropane-1,1-diphosphonic acid or a nontoxic pharmaceutically acceptable water-soluble salt were used in mouth washes and tooth pastes, the formation of tartar is greatly reduced. The pH value of the mouthwashes or tooth pastes according to the invention can vary between 5 and 9.

The following recipes are suitable as a basic formula for tooth pastes:

| | | Parts by Weight |
|---|---|---|
| (a) | Glycerin | 60.0 |
| | Water | 13.5 |
| | Sodium carboxymethyl-cellulose | 0.6 |
| | Silicic acid xero gel | 20.0 |
| | Sodium laurylsulfate | 2.0 |
| | Essential oils | 1.0 |
| | Sweetening agent | 0.4 |
| | 3-Amino-1-hydroxypropane-1,1-diphosphonic acid | 2.5 |
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silica | 1.5 |
| | Essential oils | 1.5 |
| | Sweetening agent | 0.5 |
| | 3-Amino-1-hydroxypropane-1,1- | |

-continued

|  | Parts by Weight |
| --- | --- |
| diphosphonic acid | 2.0 |

Suitable as a basic formulation for mouthwashes is the following recipe:

|  | Parts by Weight |
| --- | --- |
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| 3-Amino-1-hydroxypropane-1,1-diphosphonic acid | 2.5 |

Any one of the compounds described in Table I or a nontoxic pharmacologically acceptable water-soluble, partial or complete, salt may be substituted for the specific compound utilized; and comparable results are achieved.

By regular use of the toothpastes and/or mouthwashes containing 3-amino-1-hydroxypropane-1,1-diphosphonic acid, or its salts such as the sodium salt, the formation of tartar could be considerably reduced.

The formation of hard compact plaque on the teeth was to a great extent prevented.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A method for inhibiting the abnormal deposition or dissolution of difficultly soluble calcium salts in the mouths of warm-blooded animals, which consists essentially in applying to the teeth of said animals a pharmacologically-acceptable amino-alkanediphosphonic acid derivative selected from the group consisting of (A) at least one aminoalkane-diphosphonic acid of the formula

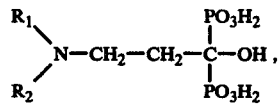

wherein $R_1$ and $R_2$ are each selected from the group consisting of hydrogen and alkyl having 1 to 3 carbon atoms, and (B) a pharmacologically-acceptable water-soluble salt of (A), said derivative being administered in the form of a dentifrice, an adherent paste, an aqueous solution, a losenge or a chewing gum containing an effective but toxicologically harmless amount therefor, in the range of about 0.01% to about 5% by weight, of said derivative.

2. A method according to claim 1 wherein said derivative is applied to the teeth of said animals as an aqueous composition having a pH in the range of 5 to 9.

3. A method for inhibiting the formation of tartar on the teeth of a warm-blooded animal, which comprises contacting said teeth with an aqueous solution having a pH of 5 to 9 and containing 0.5% to 5% by weight of an aminoalkane diphosphonic acid derivative according to claim 1.

4. A method for inhibiting the formation of tartar on the teeth of a warm-blooded animal, which comprises contacting said teeth with a dentifrice in aqueous medium having a pH in the range of 5 to 9 and containing 0.5% to 5% by weight of an aminoalkane diphosphonic acid derivatives according to claim 1.

* * * * *